(12) United States Patent
Shimizu et al.

(10) Patent No.: US 7,046,919 B2
(45) Date of Patent: May 16, 2006

(54) AROMA DIFFUSER

(75) Inventors: Satoshi Shimizu, Akashi (JP); Takao Kanba, Kobe (JP); Haruo Ishikawa, Kobe (JP); Kiyonori Itou, Nishinomiya (JP)

(73) Assignee: Matsushite Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/510,501

(22) PCT Filed: Apr. 17, 2003

(86) PCT No.: PCT/JP03/04922

§ 371 (c)(1),
(2), (4) Date: Oct. 7, 2004

(87) PCT Pub. No.: WO03/086486

PCT Pub. Date: Oct. 23, 2003

(65) Prior Publication Data

US 2005/0184045 A1     Aug. 25, 2005

(30) Foreign Application Priority Data

Apr. 18, 2002  (JP) .............................. 2002-115850
Sep. 25, 2002  (JP) .............................. 2002-278811

(51) Int. Cl.
*F24F 3/14*  (2006.01)
*F24F 6/00*  (2006.01)

(52) U.S. Cl. ...................................... 392/390; 392/393
(58) Field of Classification Search ................ 392/386, 392/390, 391, 392, 393, 394, 395, 438, 429, 392/432, 433; 239/34, 35; 422/5, 125
See application file for complete search history.

(56) References Cited

FOREIGN PATENT DOCUMENTS

| EP | 0 836 856 A | 4/1998 |
|---|---|---|
| JP | 50-126544 | 10/1975 |
| JP | 5-20575 | 9/1993 |
| JP | 3010044 | 2/1995 |
| JP | 3037625 | 3/1997 |
| JP | 3080328 | 4/2001 |

*Primary Examiner*—Sang Paik
(74) *Attorney, Agent, or Firm*—Pearne & Gordon LLP

(57) ABSTRACT

The present invention is intended to provide an aroma device that can eliminate the need for the replacement of the light source, can prevent the light source from becoming high in temperature and can allow light and aroma to be enjoyed comfortably with a sense of security for a long time. The aroma device uses, as a light source, LEDs 1 covered with first and second covers 3 and 4, and also uses a heater 5 to heat a material 10 to be heated which emits aroma; hence, the need for the replacement of the light source is eliminated, the light source is prevented from becoming high in temperature, and light and aroma can be enjoyed comfortably with a sense of security for a long time.

16 Claims, 8 Drawing Sheets

AROMA DIFFUSER

TECHNICAL FIELD

The present invention relates to an aroma device comprising a heat source.

BACKGROUND TECHNOLOGY

Hitherto, as an aroma device, there is an incense burner which comprises a saucer portion for placing an aroma material above a heat source disposed below the saucer portion.

However, since this type uses a candle or an electric bulb as a light source, there is a problem which necessitates replacement of the light source and which cannot use for a long time. In particular, in an aroma device using a candle for a light source, the light flickers and is thus visually preferred to the light of the electric bulb; however, when used for a long time, there is a problem having a high risk of causing a fire.

The conventional type has a problem that the temperature of the outer shell of its main body rises as a result of the temperature raise of a radiator plate.

The present invention is to solve the above-mentioned conventional problems, and purposes to provide an aroma device that can eliminate the need for the replacement of the light source, can prevent the light source from becoming high in temperature and can allow light and aroma to be enjoyed comfortably without anxiety for a long time.

An object of the present invention is to provide an aroma device capable of heating green tea, black tea, etc. at temperatures sufficient to emit aroma constituents therefrom while the temperature rise of the outer shell is suppressed.

DISCLOSURE OF THE INVENTION

In order to attain the above-mentioned objects, an aroma device in accordance with the present invention uses LEDs (Light Emitting Diodes) as a light source, which are covered by first and second covers, and the aroma device heats a material to be heated which emits aroma with a heater.

Hence, the need for the replacement of the light source is eliminated, the light source is prevented from becoming high in temperature, and light and aroma can be enjoyed comfortably without anxiety for a long time.

While the novel features of the invention are set forth particularly in the appended claims, the invention, both as to configuration and content, will be better understood and appreciated, along with other objects and features thereof, from the following detailed description taken in conjunction with the drawings.

Figure 1:
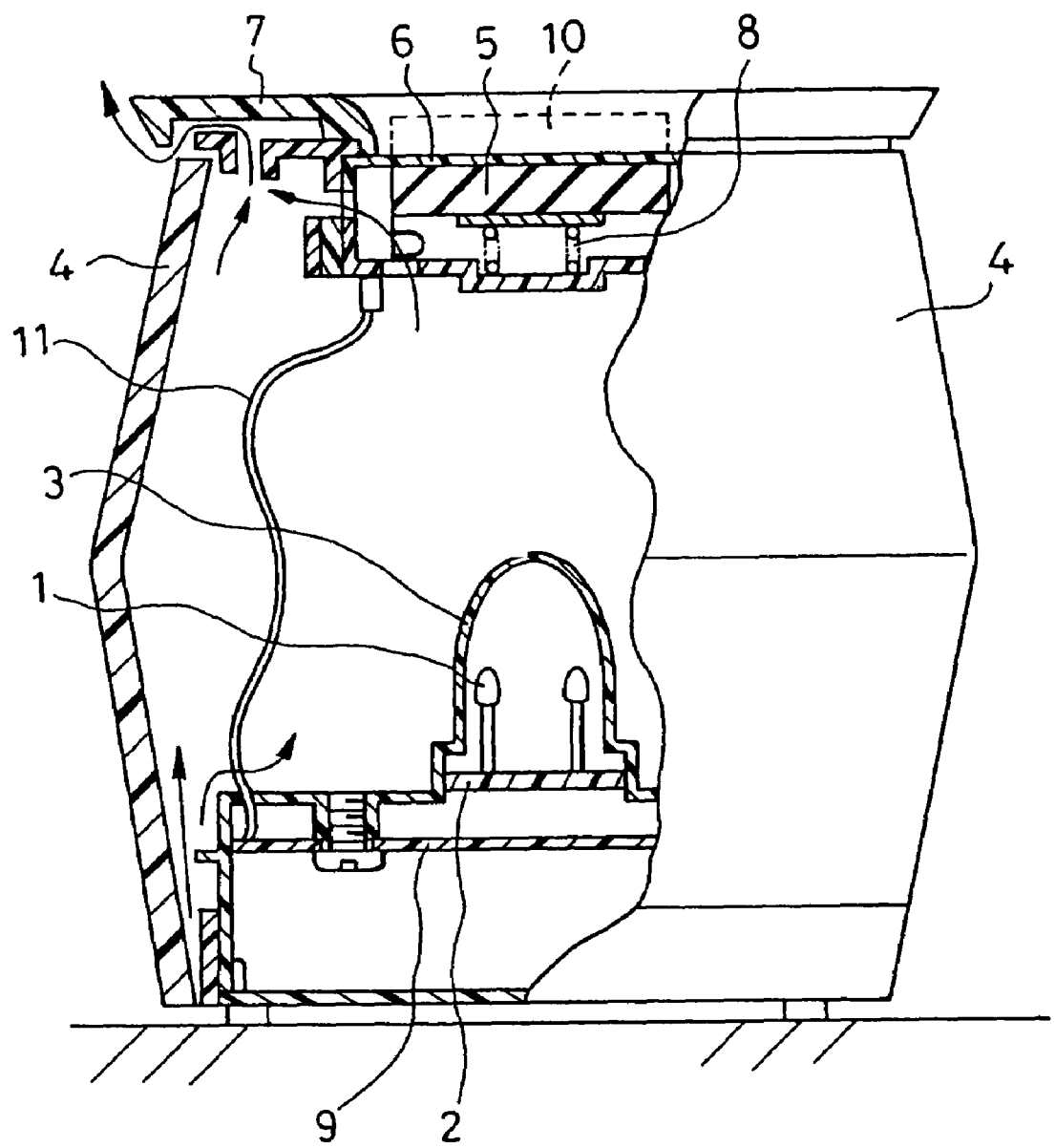
FIG. 1 is a cutaway cross-sectional view of an aroma device in accordance with Embodiment 1 of the present invention.

It will be recognized that some or all of the figures are schematic representations for purposes of illustration and do not necessarily depict the actual relative sizes or locations of the elements shown.

BEST MODES FOR CARRYING OUT THE INVENTION

An aroma device in accordance with an aspect of the present invention comprises LEDs serving as a light source, a first cover for covering the LEDs and for diffusing and transmitting light, a second cover, provided outside said first cover, for diffusing and transmitting light through at least part or the whole of the side face thereof, and a heater for heating a material to be heated which emits aroma.

Hence, the need for the replacement of the light source is eliminated, the light source is prevented from becoming high in temperature, and the light of the LEDs is produced using the first and second covers through which light is diffused and transmitted; hence, light and aroma can be enjoyed comfortably with a sense of security for a long time.

In an aroma device in accordance with another aspect of the present invention, the heater is disposed above the LEDs, and heater wires are wired from the center of the plurality of LEDs. With this configuration, light can be produced so that the light from the LEDs is not blocked by the heater wires.

An aroma device in accordance with another aspect of the present invention comprises a plurality of LEDs, and the lighting timings of which are shifted. Light is diffused inside the first cover. Furthermore, the diffused light is further diffused through the second cover and can be seen. With this configuration, the light from the LEDs being lit sequentially can be seen as blurry and faint light.

In an aroma device in accordance with another aspect of the present invention, the heater wires are bound by a holding pipe. Since the heater wires can be arranged compact, the shadows due to the heater wires can be minimized.

In an aroma device in accordance with another aspect of the present invention, the color of the holding pipe is made similar to the color of light emission of the LEDs. Hence, the shadows due to the heater wires can be further minimized.

An aroma device in accordance with another aspect of the present invention uses a heater having a PTC (Positive Temperature Coefficient) as the heater. Hence, the maximum temperature of the heater can be reduced to the Curie temperature of the heater element or less. Since the service life of the PTC heater is very long in comparison with those of conventional electric bulbs or candles, the heater can be used without replacement.

In an aroma device in accordance with another aspect of the present invention, the surface maximum temperature of the heating surface for heating the material to be heated by the heater is set in the range of 160 to 300° C. Hence, aroma constituents can be emitted from green tea, roasted green tea, etc. while the emission of burnt odor is suppressed.

In an aroma device in accordance with another aspect of the present invention, the second cover is supported in the vertical direction by a fixture member made of a transparent resin and provided inside the second cover. Hence, force application to the second cover itself in the vertical direction can be suppressed. Even in the case when the strength of the second cover made of glass is lowered by sand blasting or graining using a hydrofluoric acid or the like, strength can be securely obtained by the fixture member.

In an aroma device in accordance with another aspect of the present invention, the shape of at least the portion of the fixture member corresponding to the mounting positions of the LEDs is formed into a nearly cylindrical shape. With this configuration, the light from the side face of the second cover can be transmitted uniformly in the circumferential direction.

An aroma device in accordance with another aspect of the present invention comprises a container for accommodating the material to be heated, a heating plate disposed below the above-mentioned container, a heater for heating the above-mentioned heating plate, a supporting member, having an opening opposed to the above-mentioned heating plate, for supporting the above-mentioned heating plate and the above-mentioned heater, a second cover for forming the side face of the outer shell, and a lid cover having an opening larger than the opening in the above-mentioned supporting member, wherein the upper portion of the opening circumferential portion formed around the above-mentioned opening in the above-mentioned supporting member is fitted with the inside of the above-mentioned opening in the above-mentioned lid cover, and the upper face of the outer shell is formed of at least the opening circumferential portion of the above-mentioned supporting member, the above-mentioned heating plate and the above-mentioned lid cover. Hence, the supporting member for supporting the heater is made of a material having high heat resisting property and low thermal conductivity, whereby the thermal reliability of the configuration for supporting the heater can be raised.

In addition, although the heater and the heating plate become high in temperature, the opening circumferential portion formed around the opening in the supporting member serves as a heat insulation material, and the temperature rise is suppressed on the lid cover fitted with the circumferential portion and forming the upper face of the outer shell. Hence, the lid cover can be made of a material having low heat resisting property and has a high degree of freedom in color as a component for the outer shell, whereby the appearance is improved (components that become high in temperature during use are apt to be discolored, and they are difficult to be colored brightly). Furthermore, by the fitting between the opening circumferential portion of the supporting member and the opening in the lid cover, the upper face portion of the outer shell and the supporting member can be positioned when assembled, whereby assembly performance can be improved.

An aroma device in accordance with another aspect of the present invention comprises a container for accommodating the material to be heated, a heating plate disposed below the above-mentioned container, a heater for heating the above-mentioned heating plate, a supporting member supporting the above-mentioned heating plate and above-mentioned heater, having an opening through which the heat from the above-mentioned heating plate is transmitted to the above-mentioned container by virtue of contact or via an air layer and made of a material having thermal conductivity lower than that of the above-mentioned heating plate, a second cover for forming the side face of the outer shell, and a lid cover, having an opening through which the heat from the above-mentioned heating plate is transmitted to the above-mentioned container by virtue of contact or via an air layer, installed on the above-mentioned supporting member, and made of a material having thermal conductivity lower than that of the above-mentioned heating plate, for covering at least the outer circumferential portion of the above-mentioned supporting member and the upper portion of the above-mentioned second cover. The heat from the heater can be transmitted efficiently to the container through the opening. The heat from the heater is blocked by the supporting member having no thermal conductivity, and the heat transmitted from the heater to the supporting member is further blocked by the lid cover having no thermal conductivity. Since the heat from the heater is blocked doubly until reaching the outer shell, even if the user touches the outer shell (the lid cover and the second cover) of the aroma device, the outer shell is not so hot. The present invention realizes an aroma device capable of heating green tea, black tea, etc. to temperatures sufficient to emit aroma constituents therefrom while the temperature rise of the outer shell is suppressed.

In an aroma device in accordance with another aspect of the present invention, the above-mentioned lid cover and the above-mentioned supporting member are connected to each other in the vicinities of their respective outer circumferences. Hence, the fitting state of the opening circumferential portion of the supporting member and the opening in the lid cover is secured. Although the temperature of the inner circumferential portion of the supporting member is raised by the heater disposed in the vicinity of the center of the supporting member, the temperature of the outer circumferential portion of the supporting member is made lower than that of the inner circumferential portion by the heat resisting property of the supporting member. The conduction of the heat of the heater from the supporting member to the lid cover is small (the heat resisting property of the contact portion is high) in the vicinity of the inner circumferential portion wherein the two components are made contact, for example, by fitting, without using fastening members, but the conduction is relatively large (the heat resisting property of the contact portion is relatively low) in the vicinity of the outer circumferential portion wherein the two components are connected by fastening members. In other words, in the inner circumferential portion wherein the temperature of the supporting member is high, heat is conducted with difficulty from the supporting member to the lid cover; in the outer circumferential portion wherein heat is conducted relatively easily, the temperature of the supporting member lowers. In the present invention, the thermal conduction route from the heater to the outer shell (including the lid cover) is made as long as possible, whereby the temperature rise of the outer shell can be suppressed further.

In an aroma device in accordance with another aspect of the present invention, the opening circumferential portion of the above-mentioned opening in the above-mentioned supporting member is exposed outside through the opening in the above-mentioned lid cover. With the present invention, the heat radiation effect in the vicinity of the portion of the supporting member making contact with the heater is raised, and the temperature rise of the supporting member can be suppressed. Hence, the temperature rise of the outer shell can be further suppressed.

In an aroma device in accordance with another aspect of the present invention, the level difference at the fitting portion between the circumferential portion of the opening in the supporting member and the opening in the lid cover is made nearly zero. Hence, since there is no level difference on the surface of the outer shell, the appearance is improved, dirt hardly accumulates; even in the case when dirt accumulates, it can be removed easily.

In an aroma device in accordance with another aspect of the present invention, the above-mentioned supporting member is provided with a liquid reservoir for storing liquid entered through the clearance between the above-mentioned opening circumferential portion and the above-mentioned lid cover. There is a risk of liquid (for example, water spilled by the user) entering the clearance provided to lower thermal conduction from the heater to the outer shell. If the entered liquid enters the circuit board and the like, circuit malfunctions or trouble may be caused. With the present invention, the liquid reservoir is provided to temporarily store the entered liquid, whereby adverse effects by the liquid to the main body can be prevented.

In an aroma device in accordance with another aspect of the present invention, clearances are provided at the side face of the above-mentioned lid cover or between the above-mentioned lid cover and the above-mentioned second cover in the vicinity of the contact portion of the above-mentioned second cover and the side face of the above-mentioned lid cover and used as air ports. With the present invention, air flow is generated inside the lid cover, whereby the effect of cooling the lid cover and the supporting member is obtained. Hence, the temperature rise of the outer shell is suppressed further, and an aroma device capable of heating green tea, black tea, etc. to temperatures sufficient to emit aroma constituents therefrom can be provided.

In an aroma device in accordance with another aspect of the present invention, the above-mentioned supporting member has an upper cover and a heater cover, the above-mentioned heater cover supports the above-mentioned heater, the above-mentioned upper cover covers the above-mentioned heater, and the above-mentioned lid cover has a wall for partitioning the space between the above-mentioned air ports and the contact faces of the above-mentioned upper cover and the above-mentioned heater cover, the wall being formed to a position lower than the contact faces of the above-mentioned upper cover and the above-mentioned heater cover. If the flow of air entered through the air ports reaches the heater, the air is heated by the heater and may heat the outer shell thereafter. The present invention prevents the air entered through the air ports from passing through the contact faces of the upper cover and the heater cover and from reaching the heater. Hence, the temperature rise of the outer shell can be suppressed, and the heat of the heater can be prevented from escaping wastefully. Furthermore, adverse effects to the main body, such as that caused when liquid entered through the air ports enters the heater, can be prevented.

Embodiments of the aroma device in accordance with the present invention will be described below referring to the drawings.

EMBODIMENT 1

FIG. 1 is a vertical cross-sectional view showing the configuration of an aroma device in accordance with Embodiment 1.

In the figure, numeral 1 designates LEDs serving as a light source. Four LEDs are mounted on an LED circuit board 2 at intervals of 90 degrees (mutual angles in the case when a polar coordinate system wherein the center line (not shown) of the aroma device is used as an axis is imagined in FIG. 1 and when the intersection points (four points) between a plane perpendicular to the center line (to the face of the paper) and the LEDs 1 are represented by polar coordinates).

Numeral 3 designates a first cover for covering the LEDs 1 and for allowing light to be diffused and transmitted therethrough. Numeral 4 designates a second cover, provided outside the first cover 3, for allowing light to be diffused and transmitted through at least part or the whole of the side face thereof, and the second cover has openings at both ends in the vertical direction. In FIG. 1, the cross-sectional shapes of the first cover 3 and the second cover 4, cross-sectioned along a plane perpendicular to the face of the paper, are nearly circular or nearly regular polygonal.

Above the LEDs 1 and in the upper opening in the second cover 4, a heater 5 is provided so as to be able to heat a material 10 to be heated which emits aroma.

In other words, a heating plate 6 made of alumina is provided on the heater 5. In addition, a lid 7 which is placed over the upper opening of the second cover 4 has an opening through which the material 10 to be heated is placed on the heating plate 6 and forces the heater 5 and the heating plate 6 from above so as to secure to the second cover 4. More specifically, an integrated or separated member is mounted on the second cover 4, and the heater 5 and the heating plate 6 are forced by this member. The member forcing the heater 5 and the heating plate 6 are integrated with the lid 7, instead of being installed on the second cover 4; its configuration is not particularly limited.

In addition, a spring 8 forces the heater 5 and the heating plate 6 against the lid 7, in other words, the spring is provided between the above-mentioned member and the heater 5 and pushes the heater 5 and the heating plate 6 upward. Numeral 9 designates a control circuit board for the LEDs 1. Numeral 11 designates a heater wire for connection between the heater 5 and the control circuit board 9.

The operation of the aroma device configured as mentioned above will be described.

When a power source is turned on, 100 V AC is converted into 5 V DC by the control circuit board 9 for the LEDs 1, and the LEDs 1 mounted on the LED circuit board 2 are lit. Furthermore, by previously placing the material 10 to be heated on the heating plate 6, the material 10 to be heated is heated, and aroma is emitted from the material to be heated.

The aroma device configured as mentioned above uses the heater 5 and the LEDs 1, thereby eliminating the need for the replacement of the heat source and the light source, and being able to prevent the light source from becoming high in temperature. Furthermore, by the configuration wherein the second cover 4 through which the light from the first cover 3 is diffused and transmitted is provided outside the first cover 3 through which the light of the LEDs 1 is diffused and transmitted, the light from the LEDs 1 can be produced like a blurry flame; at the same time, occurrence of a fire owing to a flame can be prevented.

As indicated by arrows in the figure, the outside air enters the inside of the second cover 4 from the lower portion of the aroma device and is discharged from the upper circumferential fringe thereof; hence, the temperature inside the second cover 4 is maintained at about room temperature at all times.

In Embodiment 1, although alumina is used for the heating plate 6, other materials being high in thermal conductivity and superior in electric insulation may also be used; furthermore, alumina having one side surface on which the material 10 to be heated is placed is glazed or glass-processed, or a double structure comprising a metal material disposed on one side face on which the material 10 to be heated is placed and alumina disposed below the metal material is particularly excellent in antifouling and appearance quality.

In addition, in Embodiment 1, the material 10 to be heated is directly placed on the heating plate 6; however, when put in a ceramic or metallic container and used, the material 10 to be heated can easily be loaded and unloaded. Furthermore, when the bottom of the above-mentioned container is provided with holes or formed in a mesh or a grid, air convection is apt to occur, and aroma is apt to emit.

Moreover, it is desired that a compound should be used for members making contact with the heater 5 to improve thermal conductivity.

Still further, the number of LEDs 1, the voltage of the LEDs 1 and the voltage of the heater 5 are not limited particularly. In Embodiment 1, although a plurality of the LEDs 1 are used and they are simply lit, the light from the LEDs 1 can be produced like a more blurry flame by shifting the lighting timing of each.

EMBODIMENT 2

Figure 2:
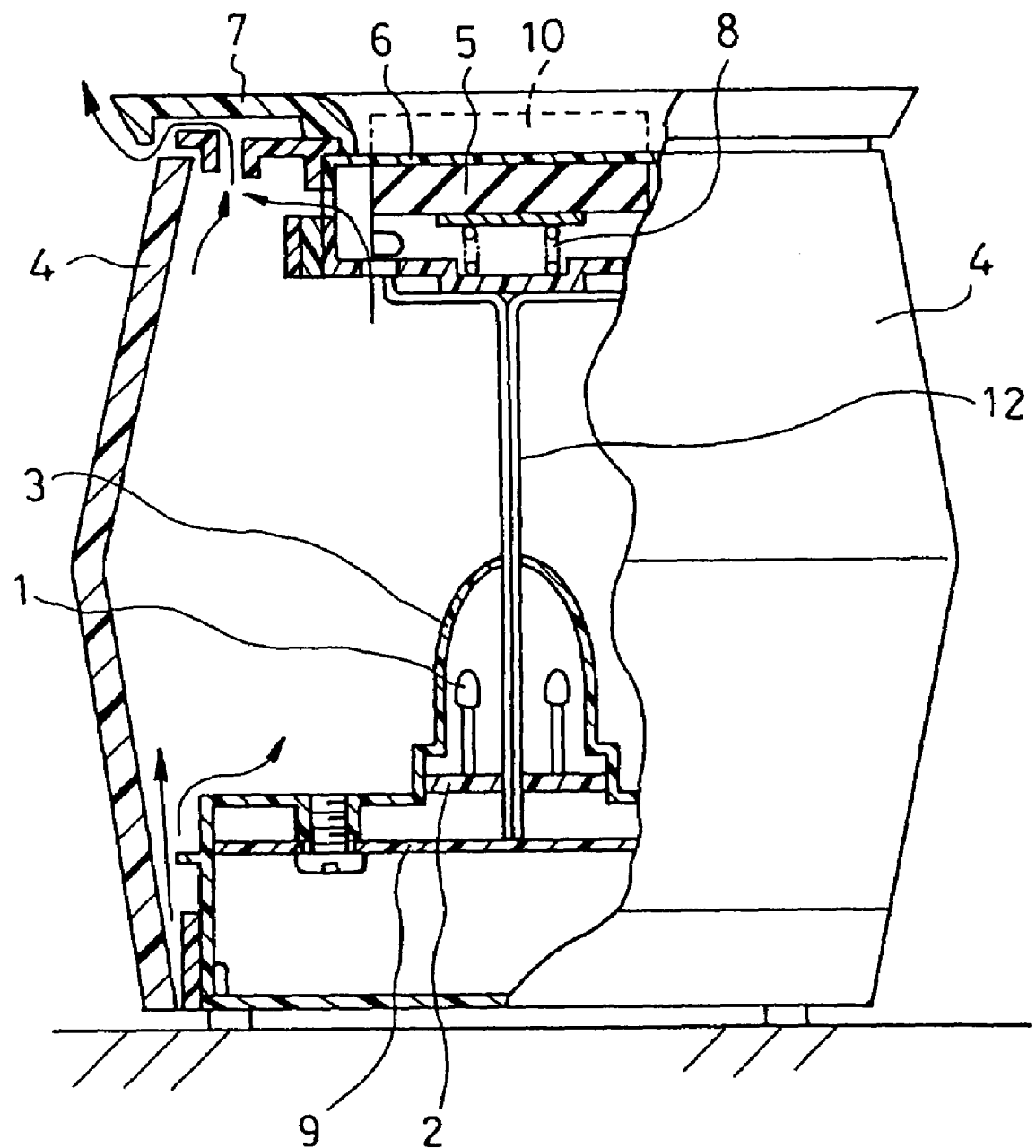
FIG. 2 is a cutaway cross-sectional view of an aroma device in accordance with Embodiment 2 of the present invention.

FIG. 2 shows an aroma device in accordance with Embodiment 2. Since the basic configuration thereof is the same as that of Embodiment 1, the same components are designated by the same numerals, their explanations are omitted, and the differences will be described mainly.

In this embodiment, LEDs 1, three in number, are mounted on an LED circuit board 2 at intervals of 120 degrees (mutual angles in the case when represented by a polar coordinate system similar to that of Embodiment 1). In addition, the upper portion of a first cover 3 through which the light of the LEDs 1 is diffused and transmitted and the LED circuit board 2 are each provided with a hole of 4 mm in diameter, and heater wires 12 pass therethrough. The heater wires 12 are raised from the center of each of the LEDs 1. A heater 5 is disposed above the LEDs 1 and connected to the heater wires 12.

The operation of the aroma device having the above-mentioned configuration is similar to that of Embodiment 1; however, since the heater wires 12 are raised from the center of each of the LEDs 1, the light of the LEDs 1 is emitted directly to the first cover 3 in any directions without being shaded by the heater wires 12. This prevents the shadows of the heater wires 12 from appearing in the light from the first cover 3.

In addition, by using the above-mentioned heater wires 12, the heater wires 12 to the heater 5 are made shortest; furthermore, the heater wires 12 can be disposed at a position farthest from the second cover 4, whereby the shadows of the heater wires 12 can be made invisible.

The holes in the upper portion of the first cover 3 and the LED circuit board 2 should only have a size capable of allowing the heater wires 12 to pass through, thereby requiring no special machining.

EMBODIMENT 3

Figure 3:
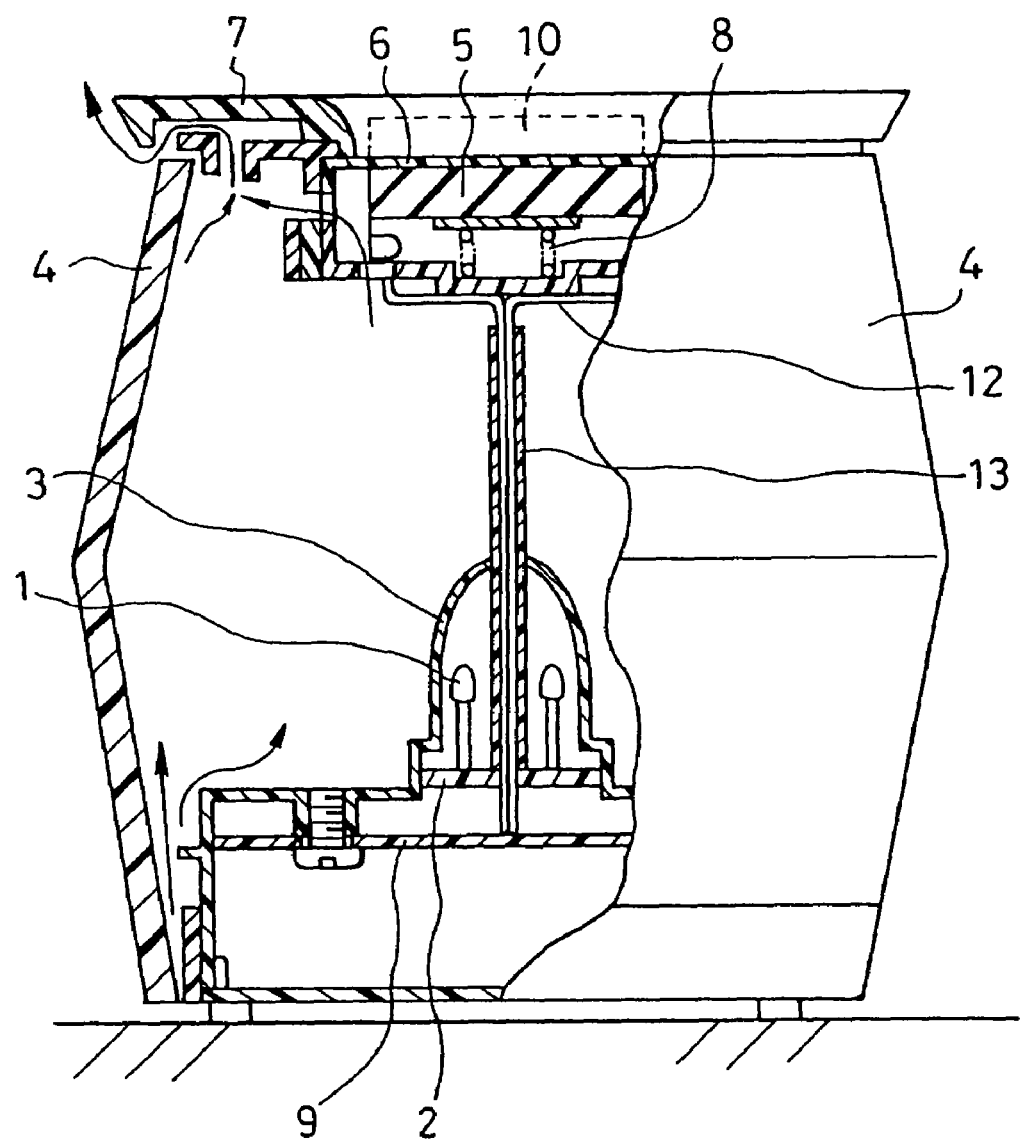
FIG. 3 is a cutaway cross-sectional view of an aroma device in accordance with Embodiment 3 of the present invention.

FIG. 3 shows an aroma device in accordance with Embodiment 3. The basic configuration thereof is the same as that of Embodiment 2. The same components are designated by the same numerals, their descriptions are omitted, and the differences will be described mainly.

Heater wires 12 raised from the center of each of LEDs 1 are bound by a holding pipe 13. In addition, a PTC heater is used as a heater 5.

In the aroma device having the above-mentioned configuration, the heater wires 12 are bundled by the holding pipe 13; hence, the heater wires 12 are formed into one and can be raised more perpendicularly, whereby the shadows due to the heater wires 12 can be made invisible.

Furthermore, by making the color of the holding pipe 13 similar to and paler than the light emission color of the LEDs 1, the shadows due to the heater wires 12 can be made further invisible.

Moreover, since a PTC heater is used as the heater 5, the temperature of the heater 5 can be prevented from rising to the Curie temperature of the heater itself or higher. Hence, the aroma device can be used more safely. In a candle type, since the distance between the candle and the heating surface changes each time or during use, it is not easy to carry out setting at the optimum surface maximum temperature; however, just as in the case of this embodiment, the surface maximum temperature of the heating surface of the heating plate 6 for heating a material 10 to be heated is set at 160° C. or more by selecting the Curie temperature of the PTC heater and by selecting the thickness and material of the heating plate 6, whereby green tea or roasted green tea can be heated, and aroma constituents can be enjoyed.

On the other hand, the temperature is set at 300° C. or less by selecting the Curie temperature of the PTC heater and by selecting the thickness and material of the heating plate 6, whereby the emission of burning odor emitted together with aroma constituents can be suppressed.

Still further, the surface maximum temperature of the heating surface of the heating plate 6 is set in the temperature range of 160° C. to 240° C., whereby aroma constituents can be emitted for a long time; hence, a temperature in the range of 160° C. to 240° C. is the most desirable as the surface maximum temperature of the heating surface.

EMBODIMENT 4

Figure 4:
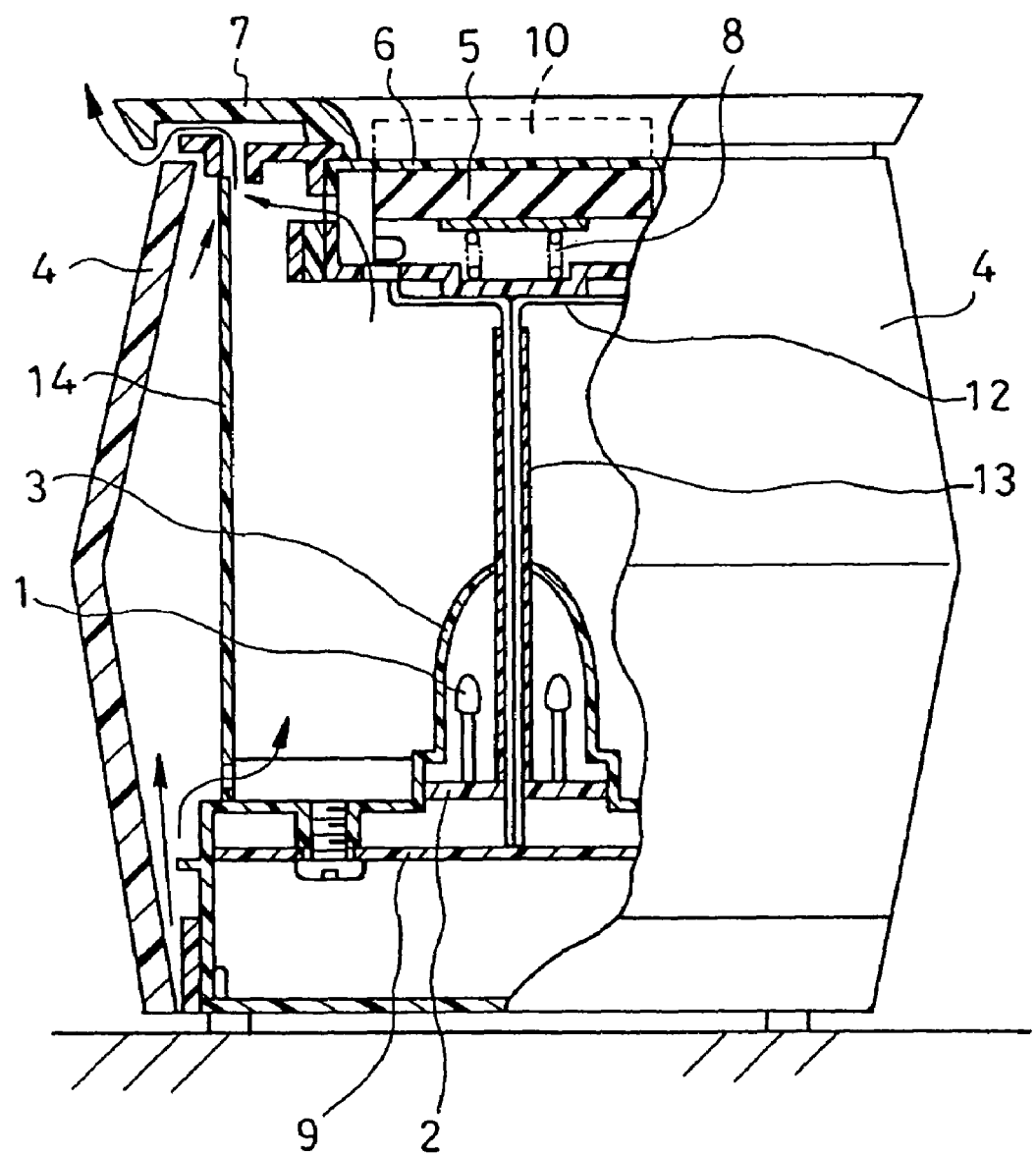
FIG. 4 is a cutaway cross-sectional view of an aroma device in accordance with Embodiment 4 of the present invention.

FIG. 4 shows an aroma device in accordance with Embodiment 4. Since the basic configuration thereof is the same as those of Embodiments 1 to 3, the same components are designated by the same numerals, their descriptions are omitted, and the differences will be described mainly.

This embodiment is configured such that the load applied to the second cover 4 in the vertical direction is supported by a fixture member (a column in the case of this embodiment) 14 made of a transparent polycarbonate resin and provided inside the second cover 4. Furthermore, the shape of at least the portion of the fixture member (column) 14 corresponding to the mounting positions of the LEDs 1 is formed into a nearly cylindrical shape. The whole of the fixture member (column) 14 in accordance with Embodiment 4 has a nearly cylindrical shape.

In this kind of aroma device, the fixture member (column) 14 made of a transparent polycarbonate resin is used to support the second cover 4 made of glass in the vertical direction, whereby the force applied to the glass can be reduced without adversely affecting the light of the LEDs 1.

In addition, the fixture member (column) 14 may be made of any material which can support the glass in the vertical direction and is transparent; however, since it is disposed in the vicinity of the heater 5, it is desired to be made of a polycarbonate resin having high heat resisting property.

Furthermore, the shape of the fixture member (column) 14 may be any shape which does not adversely affect the light of the LEDs 1 due to the refraction of light by the fixture member (column); however, a nearly cylindrical shape wherein the light from the first cover 3 can be transmitted uniformly is best suited. Still further, the fixture member (column) 14, serving as an internal structural member, can be provided with functions other than the supporting function; however, at least the portion corresponding to the mounting positions of the LEDs 1 is preferably made nearly cylindrical, because the light from the side face of the second cover 4 can be transmitted uniformly.

The configurations in accordance with the above-mentioned Embodiments 1 to 4 are not limited to their respective individual configurations; it is needless to say that they can be combined appropriately to obtain configurations.

EMBODIMENT 5

Figure 5:
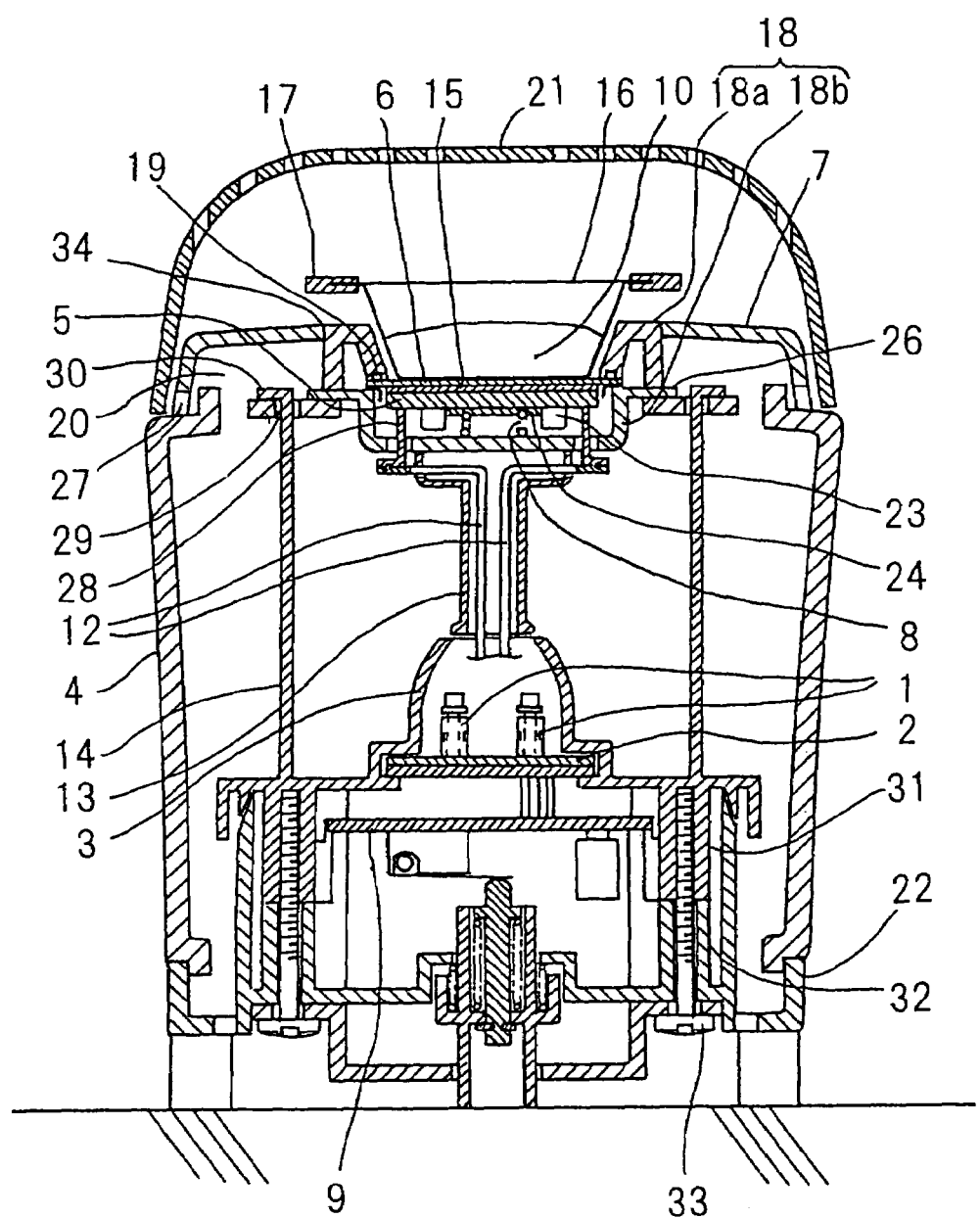
FIG. 5 is a cross-sectional view of an aroma device in accordance with Embodiment 5 of the present invention.
Figure 6:
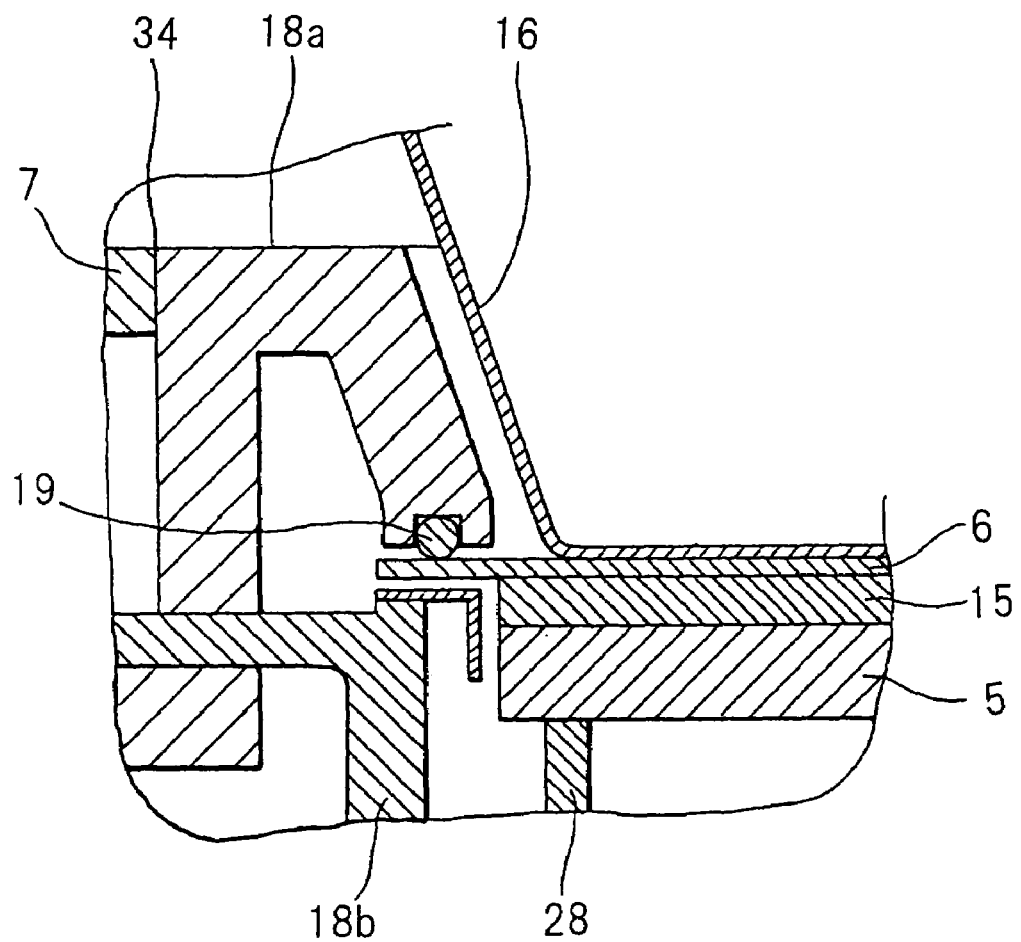
FIG. 6 is a cross-sectional view of a partially enlarged cross-sectional view of the aroma device in accordance with Embodiment 5 of the present invention.
Figure 7:
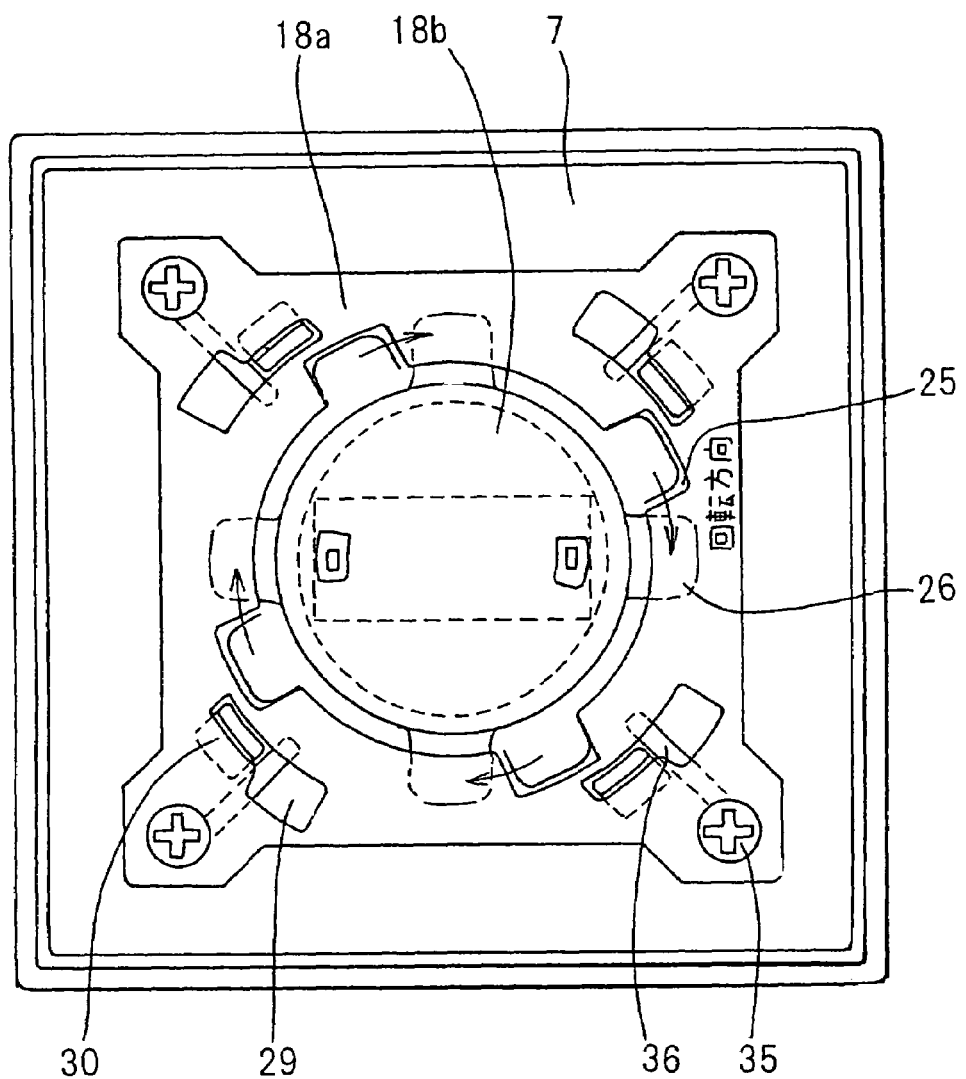
FIG. 7 is a bottom view of the heater unit of the aroma device in accordance with Embodiment 5 of the present invention.

An aroma device in accordance with Embodiment 5 of the present invention will be described using FIGS. 5 to 7. FIG. 5 is a cross-sectional view of the aroma device in accordance with Embodiment 5 of the present invention, taken along the perpendicular plane passing through the center thereof. FIG. 6 is a partially enlarged cross-sectional view of FIG. 1. FIG. 7 is a bottom view of a heater unit.

Numeral 5 designates a PTC heater having a self-temperature control function using a device having a Curie temperature of 260° C. A conduction plate A 15 is placed on the heater 5. The conduction plate A 15 is made of a material (aluminum in the case of this embodiment) having high heat resisting property and high thermal conductivity. A heating plate 6 is placed on the conduction plate A 15. The heating plate 6 serves to transmit heat from the heater 5 to a container 16. If heat radiation from the heating plate 6 becomes excessive, the heating temperature of a material to be heated (tea leaves or the like in the case of this embodiment) lowers. The heating plate 6 employs a material (stainless steel in the case of this embodiment) having high heat resisting property and high thermal conductivity as an absolute value, which is relatively lower than the thermal conductivity of the material of the conduction plate A 15. Furthermore, it is preferable that the heating plate 6 should have rust resistance, whereby its beautiful appearance is maintained after being used for a long time. A compound (thermal diffusion material) is applied (the compound is not shown) between the heater 5 and the conduction plate A 15 and between the conduction plate A 15 and the heating plate so as to improve thermal conduction.

Numeral 16 designates a container containing an appropriate amount of the tea leaves of green tea or the like serving as a material to be heated, and being placed on the heating plate 6. The container 16 has an accommodation portion, the planar shape of which is square, and a handle portion 17 disposed around the accommodation portion. The accommodation portion of the container 16 is made of a material (stainless steel in the case of this embodiment) having high heat resisting property, high thermal conductivity and high rust resistance. The handle portion 17 of the container 16 is made of a material (resin in the case of this embodiment) having high heat resisting property and low thermal conductivity.

Numeral 18 designates a supporting member for covering the heater 5 and the heating plate 6, and it comprises an upper cover 18a (having an opening through which the heat from the heating plate 6 is transmitted to the container 16 by virtue of contact or via an air layer) for carrying out covering from above and a heater cover 18b for carrying out covering from below. Numeral 19 designates a packing made of silicone rubber and provided between the heating plate 6 and the upper cover 18a, and it prevents liquid (water or the like spilled from a cup) dropped onto the heating plate 6 from entering the inside of the aroma device. The packing 19 is made of a material having high heat resisting property, low thermal conductivity and predetermined elasticity.

Since the upper cover 18a and the heater cover 18b serves to cover the heater 5 and also serves to prevent the temperature rise of the lid cover 7 serving as the outer shell of the aroma device (so that the user does not feel hot even when he touches the outer shell of the aroma device), they are made of a material (PPS (polyphenylene sulfide) resin in the case of this embodiment) having high heat resisting property and low thermal conductivity. The color of the PPS resin is desired to be dark so that discoloration owing to high temperatures can be prevented; black is used in the case of Embodiment 5.

Numeral 7 designates a lid cover having a hole fitted with the upper portion of the upper cover 18a and having an opening (larger than the opening in the supporting member 18) through which the heat from the heating plate is transmitted to the container 16 by virtue of contact or via an air layer. The lid cover 7 is made of a material having low thermal conductivity (for example, PET (polyethylene terephthalate) resin, PBT (polybutylene terephthalate) resin or a mixture of PET resin and PBT resin). The lid cover 7 and the upper cover 18a are secured with screws (screws 35 shown in FIG. 7) serving as fastening means at four positions of the outer circumferential portion (at the corner portions in the case of this embodiment). The lid cover 7 and the upper cover 18a make contact with each other in the vicinities of their internal circumferences and are fitted at the fitting portion 34.

Numeral 20 designates a space defined by the supporting member 18 and the lid cover 7.

Numeral 4 designates a second cover (body) for forming the outer shell of the main body. The second cover 4 is made of a transparent material (resin in the case of this embodiment) having low thermal conductivity. The lid cover 7 covers the upper opening in the second cover 4. A plurality of air ports 27 are formed by cutting a part of the end face of the lid cover 7 in the vicinity of the contact portion between the second cover 4 and the side face of the lid cover 7. The side face of the lid cover 7 may be provided with a plurality of air ports.

An outer lid guard 21 is provided above the second cover 4, and a bottom portion 22 is provided below the second cover 4. The outer lid guard 21 is made of a material having low thermal conductivity (for example, PET resin, PBT resin or a mixture of PET resin and PBT resin) and has a plurality of air ports for allowing air including aroma to pass through.

Numeral 24 designates a conduction plate B provided between a heater spring 8 and the heater 5, and it maintains thermal uniformity at the lower face of the heater 5.

The upper cover 18a is further provided with fixture plates 23 formed of four projections projecting downward and fitting hole portions 29. The fixture plates 23 are used to position the conduction plate B 24, the heater 5 and the conduction plate A 15 in the horizontal direction.

Numeral 8 designates one coiled heater spring, both ends of which make contact with the conduction plate B 24 and the heater cover 18b, respectively. One end of the heater spring 8 is inserted into a dent portion provided in the heater cover 18b so that its installation position is not dislocated. The heater spring 8 applies force to the conduction plate B 24, the heater 5 and the conduction plate A 15 upward to force them against the heating plate 6. The heater spring 8 and the heating plate 6 are used to determine the vertical positions of the conduction plate B 24, the heater 5 and the conduction plate A 15.

Four legs 26 provided on the heater cover 18b are inserted, from below, into four insertion holes 25 provided in the upper cover 18a, rotated and guided to positions away from the insertion holes 25, and then held by the upper cover 18a. The heater spring 8 applies force to the legs 26 of the heater cover 18b downward to force them against the upper cover 18a. The heater spring 8 and the upper cover 18a are used to determine the vertical position of the heater cover 18b.

The heater unit is formed by the conduction plate B 24, the heater 5, the conduction plate A 15, the heating plate 6, the upper cover 18a, the heater cover 18b, the lid cover 7, etc.

A column unit is a resin molding of an integral structure having legs 30, a cylindrical column (fixture member) 14 and a column boss 31. The four legs 30 provided on the column unit are inserted, from below, into the wide-width portions of the four fitting hole portions 29 provided in the upper cover 18a, rotated and guided to the narrow-width portions of the fitting hole portions 29, and then held by the upper cover 18a. When the lid cover 7 is installed on the upper cover 18a using screws 35, rotation stoppers 36 which are projections provided on the lid cover 7 prevent the legs 30 of the column unit from disconnection from the narrow-width portions of the fitting hole portions 29. Hence, the heater unit and the column unit are assembled integrally. The legs 30 of the column unit can move slightly inside the narrow-width portions of the fitting hole portions 29 but they are not disconnected.

The bottom portion 22 has a bottom boss 32. In the present specification, the whole of the portions (excluding screws 33, a circuit board 9 and a light-emitting portion 1) positioned below the column unit and the second cover 4 is collectively referred to as the bottom portion 22. The bottom portion 22 supports a plurality of LEDs (light-emitting portion) 1, a control circuit board (circuit board) 9 for driving the heater 5 and for turning on the light-emitting portion 1, the heater unit and the column unit.

In the state that the second cover 4 is held between the heater cover 18b and the bottom portion 22, the heater unit and the column unit are mounted on the bottom portion 22 by connecting the bottom boss 32 to the column boss 31 by the screws 33. The column (fixture member) 14 mounted by the screws 33 supports the heater unit together with the second cover 4 made of glass. The whole structure of the aroma device is thus secured. It is preferable that the height of the column (fixture member) 14 should be slightly higher than the height of the second cover 4. With this structure, the column (fixture member) 14 substantially supports the heater unit, and almost no load is applied to the second cover 4 made of glass. Even in the event that the second cover 4 is broken by an impact from outside while the aroma device is used, the aroma device is prevented from being broken into pieces. The heater being hot is prevented from being removed from the aroma device and from rolling. The aroma device is displayed in a room and the aroma therefrom is enjoyed. In addition to performing a practical function of emitting pleasant aroma, the aroma device is required to be an attractive decorative ornament in the room. Generally speaking, fastening screws that can be seen from outside significantly impair the decorative appeal of products. With the above-mentioned structure of the aroma device in accordance with the present invention, the whole structure is secured using the plurality of screws 33 attached to the bottom. Since no screws are exposed outside, the aroma device in accordance with the present invention placed on a shelf has an attractive decorative appearance.

The whole of the aroma device is assembled as described above. The upper face of the outside of the assembled aroma device is formed of the opening circumferential portion of the supporting member 18, the heating plate 6 and the lid cover 7. The opening circumferential portion of the supporting member 18 is exposed outside through the opening in the lid cover 7. During use, the outer lid guard 21 is further placed thereon.

The heater 5 is provided with electrodes 28, and current flows through the heater 5 when a power switch provided on the main body of the aroma device is turned on.

The operation of the aroma device in accordance with Embodiment 5 configured as described above will be described. The container 16 supplied with an appropriate amount of green tea is placed on the heating plate 6, and the power switch is turned on, whereby the heater 5 is heated, and the heat of the heater 5 is efficiently transmitted to the heating plate 6 and the accommodation portion of the container 16, made of metals, via the conduction plate A 15 having excellent thermal conductivity; hence, aroma constituents are emitted from the green tea. The flow of air including the aroma constituents reaches the user via the plurality of air ports in the outer lid guard 21.

The portion of the upper cover 18a corresponding to the circumference (the circumferential portion of the opening in the upper cover 18a (the opening circumferential portion)) above the heating plate 6 is fitted inside the opening in the lid cover 7, whereby the rest portion of the upper cover 18a is covered with the lid cover 7 while the heat of the heater 5 is prevented from staying inside the main body; hence, the temperature of the lid cover 7, which is the upper portion of the main body and touched with a human hand, can be lowered. Therefore, in Embodiment 5, PET resin, PBT resin, excellent in gloss, or a mixture of PET resin and PBT resin can be used for the lid cover 7.

In addition, by lowering the temperature of the lid cover 7 and the internal temperature of the main body, the temperature rise of the second cover 4 serving as the outer shell is suppressed. Furthermore, by covering the heater 5 with the upper cover 18a and the heater cover 18b just as in the case of Embodiment 5, the ambient temperature inside the outer shell is suppressed, whereby the temperature of the second cover serving as the outer shell and the temperature of the lid cover 7 covering the upper portion of the above-mentioned second cover can be lowered.

Furthermore, the space 20 is formed between the lid cover 7 and the supporting member 18, whereby heat conducted from the supporting member 18 to the lid cover 7 can be made small, and the temperature rise of the outer shell can be suppressed.

Although the PTC heater is used as the heater 5 in Embodiment 5; however, in the case of the configuration in accordance with Embodiment 5, even if any kind of heater is used, heating can be carried out up to temperatures sufficient to emit aroma constituents from green tea, black tea, etc., and the temperature rise of the outer shell can be suppressed.

Still further, although the heat of the heater 5 is transmitted to the heater spring 8 and then transmitted to the heater cover 18b, since a coiled spring is used for the heater spring 8, heat conduction to the heater cover 18b is suppressed. Even if other springs, such as a leaf spring, are used only to apply force to the heater 5, the same effect can be obtained.

In Embodiment 5, the upper cover 18a is fitted with the heater cover 18b without using screws; however, they may further be fastened with screws after the fitting, or they can be assembled only by fastening with screws without insertion or rotation.

EMBODIMENT 6

Figure 8:
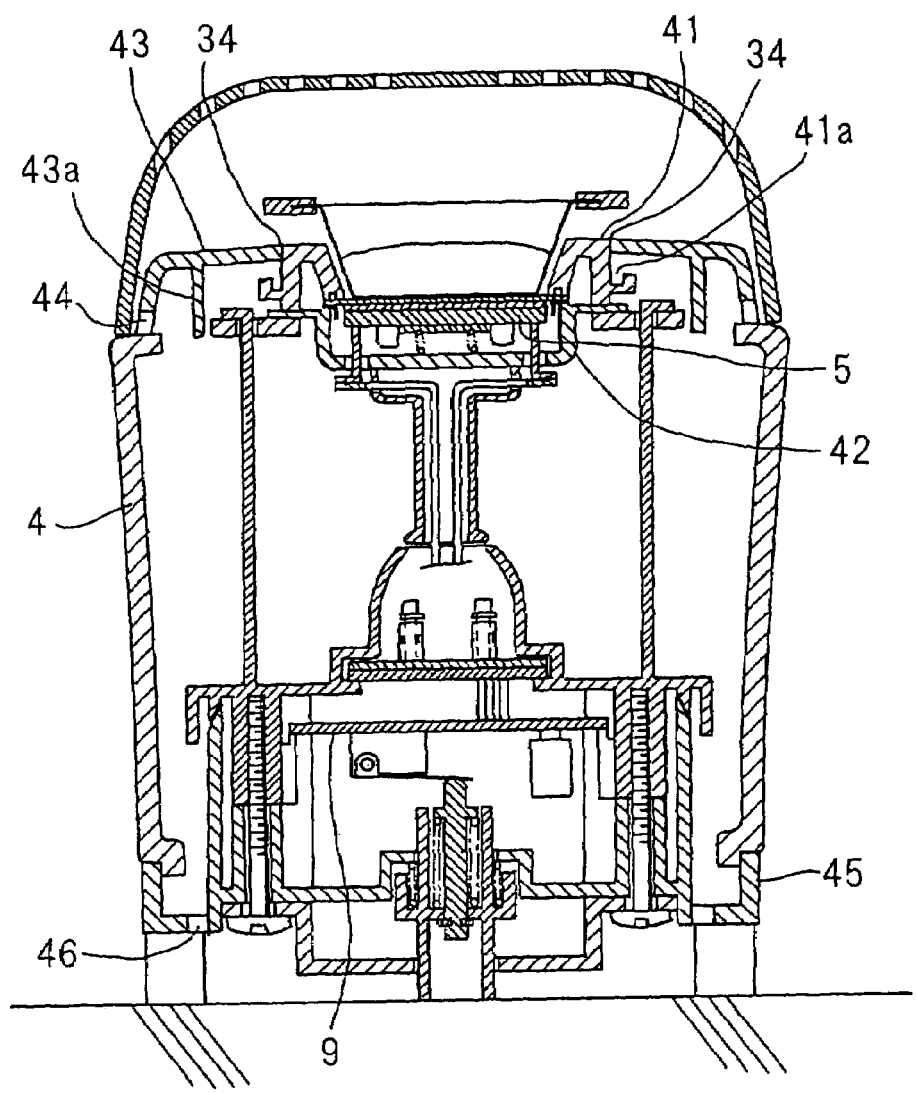
FIG. 8 is a cross-sectional view of an aroma device in accordance with Embodiment 6 of the present invention.

An aroma device in accordance with Embodiment 6 of the present invention will be described using FIG. 8. FIG. 8 is a cross-sectional view taken along a perpendicular plane passing through the center of the aroma device in accordance with Embodiment 6 of the present invention.

Numeral 41 designates an upper cover for covering the heating plate from above. Numeral 42 designates a heater cover for covering the heating plate from below. Numeral 43 designates a lid cover fitted with the upper cover; at the central portion of the side end of the lid cover 43, air ports 44 are provided, and a wall 43a is also provided at a position inside from the air ports 44 (at a position wherein the space between the air ports 44 and the contact faces of the upper cover 41 and the heater cover 42 is partitioned). The wall 43a is formed to a position lower than the contact faces (the fitting faces in this embodiment) of the upper cover 41 and the heater cover 42. The air ports are provided in the side face of the lid cover 43 or the contact portions of the second cover 4 and the side face of the lid cover 43.

Numeral 45 designates a bottom plate, and it has air ports 46. The upper cover 41 is provided with a liquid reservoir 41a which accumulates liquid such as water entered through the clearance between the upper cover 41 and the lid cover 43. In the other respects, the aroma device in accordance with Embodiment 6 is similar to that in accordance with Embodiment 5.

The aroma device in accordance with Embodiment 6 carries out operation nearly similar to that of Embodiment 5. The aroma device in accordance with Embodiment 6 can dissipate the heat of the air inside the main body through the air ports 44, whereby the temperature of the second cover 4 serving as the outer shell can be lowered.

In addition, in the case when liquid (water, for example) enters through the air ports, the entered liquid strikes against the wall 43a provided on the lid cover 43 and drops downward. Since the lower end of the wall 43a is positioned so as to be lower than the contact faces of the upper cover 41 and the heater cover 42, even if the entered liquid spurts speedily in the horizontal direction from the lower end of the wall 43a, there is no risk of the liquid passing through the clearance between the upper cover 41 and the heater cover 42 and reaching the heater 5. The wall 43a can prevent the entered liquid form adversely affecting the components disposed inside the main body, such as the heater.

At the fitting portion 34 between of the upper cover 41 and the lid cover 43, by contacting them with each other so that the clearance therebetween is made small, even if water is poured over the clearance (fitting portion) 34 by mistake, the amount of water entering the inside through the clearance is small (it is difficult to completely prevent the entry of water). The liquid reservoir 41a provided on the upper cover 41 can temporarily accumulate water entered inside. The accumulated water can be evaporated gradually while the aroma device is used or left unused. Hence, adverse effects to the main body (for example, malfunctions or trouble caused by water having reached the circuit board 9) can be prevented. The effect of providing the liquid reservoir 41a is significant. Furthermore, by making the level difference between both sides of the fitting portion 34 nearly zero, water hardly accumulates and dirt hardly gathers.

As clarified by the above-mentioned embodiments, in accordance with the aroma device of the present invention, the need for the replacement of the light source is eliminated, the light source is prevented from becoming high in temperature, and the light of the LEDs is produced using the first and second covers through which light is diffused and transmitted; hence, light and aroma can be enjoyed comfortably with a sense of security for a long time.

According to the present invention, the aroma device capable of heating green tea, black tea, etc. to temperatures sufficient to emit aroma constituents can be provide while the temperature rise of the outer shell is suppressed.

According to the present invention, liquid is not almost allowed to enter through the clearance between the upper cover, or the component such as a heater disposed inside the main body can be prevented from harmful influence of entered liquid.

According to the present invention, the main body can be prevented from harmful influence due to liquid entered through the air ports provided in the lid cover and the like.

Although the present invention has been described with respect to its preferred embodiments in some detail, the disclosed contents of the preferred embodiments may change in the details of the structure thereof, and any changes in the combination and sequence of the components may be attained without departing from the scope and spirit of the claimed invention.

INDUSTRIAL APPLICABILITY

The present invention is useful as an aroma device for allowing aroma to be enjoyed.

The invention claimed is:

1. An aroma device comprising visible light emitting diodes (LEDs) as a light source, a first cover for covering said LEDs and for diffusing and transmitting light, a second cover, provided outside said first cover, for diffusing and transmitting light at least part or the whole of the side face of said second cover, and a heater for heating a material to be heated which emits aroma, wherein
    said heater is disposed above said LEDs, and heater wires are wired from the center of the plurality of LEDs.

2. An aroma device in accordance with claim 1, wherein a plurality of LEDs are provided, and respective lighting timings are shifted.

3. An aroma device in accordance with claim 1, wherein said heater wires are bundled by a holding pipe.

4. An aroma device in accordance with claim 3, wherein the color of said holding pipe is made similar to the color of emitted light of said LEDs.

5. An aroma device in accordance with claim 1, wherein a heater having a positive temperature coefficient (PTC) is used as said heater.

6. An aroma device in accordance with claim 1, wherein a heating plate is disposed between the material to be heated and said heater, and a surface maximum temperature of a heating surface of the heating plate being set to 160–300° C.

7. An aroma device in accordance with claim 1, wherein said second cover is supported in the vertical direction by a fixture member made of a transparent resin and provided inside said second cover.

8. An aroma device in accordance with claim 7, wherein the shape of at least the portion of said fixture member corresponding to the mounting positions of said LEDs is formed into a nearly cylindrical shape.

9. An aroma device comprising
    visible light emitting diodes (LEDs) as a light source, a first cover for covering said LEDs and for diffusing and transmitting light, a second cover, provided outside said first cover, for diffusing and transmitting light at least part or the whole of the side face of said second cover, and a heater for heating a material to be heated which emits aroma, said aroma device further comprising:

a container for accommodating the material to be heated which emits aroma, a heating plate disposed below said container, said heater for heating said heating plate, a supporting member, having an opening opposed to said heating plate, and for supporting said heating plate and said heater, said second cover for forming a side face of the outer shell of the aroma device, and a lid cover having an opening larger than the opening in said supporting member, wherein an opening circumferential portion is formed around said opening in said supporting member, an upper portion of the opening circumferential portion is fitted to the inside of said opening in said lid cover, and the upper face of the outer portion is formed of at least the opening circumferential portion of said supporting member, said heating plate and said lid cover.

10. An aroma device in accordance with claim 9, wherein said lid cover and said supporting member are connected to each other by fastening members in the vicinities of their respective outer circumferences.

11. An aroma device in accordance with claim 9, wherein the opening circumferential portion of said opening in said supporting member is exposed outside through the opening in said lid cover.

12. An aroma device in accordance with claim 9, wherein the level difference at the fitting portion between the circumferential portion of the opening in said supporting member and the opening in said lid cover is made nearly zero.

13. An aroma device in accordance with claim 9, wherein clearances are provided at the side face of said lid cover or between said lid cover and said second cover in the vicinity of the contact portion of said second cover and the side face of said lid cover and are allocated for air ports.

14. An aroma device in accordance with claim 13, wherein said supporting member has an upper cover and a heater cover, said heater cover supports said heater, and said upper cover covers said heater, and said lid cover has a wall for partitioning the space between said air ports and the contact faces of said upper cover and said heater cover, said wall being formed to a position lower than the contact faces of said upper cover and said heater cover.

15. An aroma device comprising visible light emitting diodes (LEDs) as a light source, a first cover for covering said LEDs and for diffusing and transmitting light, a second cover, provided outside said first cover, for diffusing and transmitting light at least part or the whole of the side face of said second cover, and a heater for heating a material to be heated which emits aroma, said aroma device further comprising:

a container for accommodating the material to be heated which emits aroma, a heating plate disposed below said container, said heater for heating said heating plate, a supporting member for supporting said heating plate and said heater, said supporting member having an opening through which heat from said heating plate is transmitted to said container by virtue of contact or via an air layer and made of a material having thermal conductivity lower than that of said heating plate, said second cover for forming the side face of an outer shell of the aroma device, and a lid cover, having an opening through which the heat from said heating plate is transmitted to said container by virtue of contact or via an air layer, said lid cover being mounted on said supporting member and covering at least the outer circumferential portion of said supporting member and the upper portion of said second cover, being made of a material having thermal conductivity lower than that of said heating plate.

16. An aroma device in accordance with claim 11, wherein said supporting member is provided with a liquid reservoir for storing liquid entered through the clearance of fitting portion of said opening circumferential portion and said lid cover.

* * * * *